United States Patent [19]

Risch et al.

[11] 4,369,131

[45] Jan. 18, 1983

[54] ENHANCED CATALYST STABILITY FOR CYCLIC CO METHANATION OPERATIONS

[75] Inventors: Alan P. Risch, New Fairfield, Conn.; Jule A. Rabo, Armonk, N.Y.

[73] Assignee: Union Carbide Corporation, Danbury, Conn.

[21] Appl. No.: 229,998

[22] Filed: Jan. 30, 1981

[51] Int. Cl.³ .......................... B01J 23/78; B01J 21/08
[52] U.S. Cl. .............................. 252/459; 252/455 R; 48/197 R; 585/733
[58] Field of Search .................. 252/459, 455 R; 48/197 R; 585/733

[56] References Cited

U.S. PATENT DOCUMENTS

| | | | |
|---|---|---|---|
| 2,941,958 | 6/1960 | Connor, Jr. et al. | 252/459 X |
| 3,047,630 | 7/1962 | Addy | 252/459 X |
| 3,417,029 | 12/1968 | McMahon | 252/459 X |
| 3,432,443 | 3/1969 | Davies et al. | 252/459 |
| 3,988,262 | 10/1976 | Andersen et al. | 252/466 |
| 3,988,263 | 10/1976 | Hansford et al. | 252/466 |
| 4,032,556 | 6/1977 | Banks | 260/449 |
| 4,242,103 | 12/1980 | Rabo et al. | 48/197 R |

*Primary Examiner*—Carl F. Dees
*Attorney, Agent, or Firm*—Alvin H. Fritschler

[57] ABSTRACT

Carbon monoxide-containing gas streams are passed over a catalyst to deposit a surface layer of active surface carbon thereon essentially without the formation of inactive coke. The active carbon is thereafter reacted with steam or hydrogen to form methane. Enhanced catalyst stability for long term, cyclic operation is obtained by the incorporation of an alkali or alkaline earth dopant in a silica binding agent added to the catalyst-support additive composition.

28 Claims, 3 Drawing Figures

ENHANCED CATALYST STABILITY FOR CYCLIC CO METHANATION OPERATIONS

STATEMENT

The Government of the United States of America has rights pursuant to Contract No. DE-AC03-78CS40177 awarded by the Department of Energy.

BACKGROUND OF THE INVENTION

1. Field of the Invention

The invention relates to the production of methane from carbon monoxide. More particularly, it relates to the preparation of a catalyst formulation of enhanced stability for use in such methanation operations.

2. Description of the Prior Art

The production of low-cost methane as a replacement for natural gas has been the subject of considerable interest in light of the energy requirements of industrial societies throughout the world. The COthane process has been developed in response to such interest and concerns. This process, disclosed in detail in U.S. Pat. No. 4,242,103, is a cyclic, essentially two-step process in which a surface layer of active surface carbon is deposited on a catalyst and is then contacted with steam or hydrogen to convert the active surface carbon to methane and carbon dioxide. The process is repeated in cyclic operations without the need for regenerating the catalyst as a necessary additional step of the cyclic operation.

The disproportionation catalyst used for the COthane process is employed essentially in its metal state and is typically combined with a catalyst support additive and with a binder to ensure that the catalyst has a desired combination of activity, capacity and stability. In the absence of such additives and binders, the preferred catalyst, nickel, for example, is relatively unstable and tends to agglomerate and sinter with resultant reduction of its surface area. With the incorporation of additives and binders into the catalyst formulation, on the other hand, agglomeration and sintering of the catalyst is prevented, and the activity and capacity of the catalyst, and its stability in continuous, cyclic operations can be maintained.

Those skilled in the art will appreciate that the long term stability of the catalyst composition employed in the cyclic COthane process will have a significant effect on the overall technical and economic feasibility of the process for the production of low-cost methane from CO-containing waste gas streams. During repeated use in the cyclic process, the disproportionation catalyst tends to become coated with inactive carbon that eventually reduces the efficiency of the catalyst to the point where its regeneration becomes necessary or desirable. By extending the number of cycles of use of the catalyst between regenerations, the cost of the overall operation can be reduced, facilitating the practice of the COthane process in practical, commercial operations. It is highly desirable in the art, therefore, that the long term stability of the catalyst composition be improved so as to enable the catalyst to be employed satisfactorily in the cyclic COthane process over an extended number of cycles before burn off or other removal of the inactive carbon becomes necessary or desirable.

It is the object of the invention, therefore, to provide an improved disproportionation catalyst for use in the COthane process.

It is another object of the invention to provide a process for the production of a disproportionation catalyst having enhanced stability in long term cyclic operations.

It is a further object of the invention to provide a catalyst having enhanced stability for continuous use in the cyclic COthane process.

With these and other objects in mind, the invention is hereinafter described in detail, the novel features thereof being particularly pointed out in the appended claims.

SUMMARY OF THE INVENTION

Enhanced catalyst stability for long term cyclic operation of the COthane process is achieved by incorporating an alkali or alkaline earth additive into the binder prior to the mixing of the binder with the pre-formed catalyst-catalyst support additive composition. The resulting catalyst formulation can be readily employed in the cyclic process over an extended number of processing cycles with stable methane production and with a low level of inactive carbon residue formation. The need for regeneration of the catalyst is thereby reduced, and the catalyst can be employed for a desirably longer number of processing cycles before regeneration becomes necessary or desirable.

DETAILED DESCRIPTION OF THE INVENTION

Figure 1:
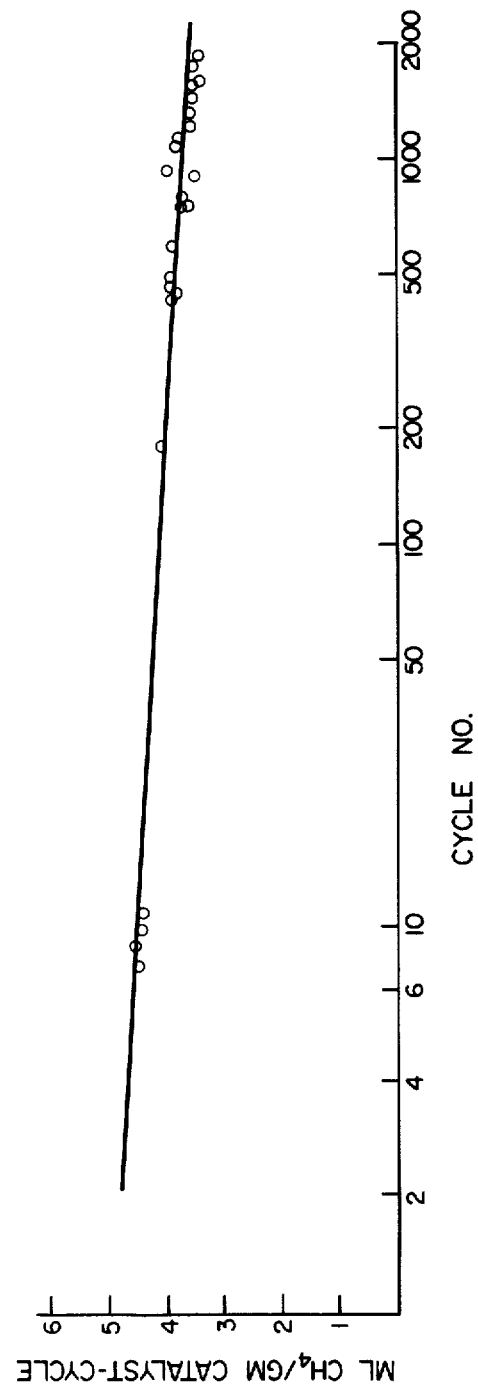
FIG. 1 is a plot showing the methane production per unit of catalyst over the course of an extended number of cycles of the Cothane process using sodium as the dopant material added to the binder in accordance with the practice of the invention.

The objects of the invention are accomplished, surprisingly, by the incorporation of a dopant into the binder prior to the mixing of the binder with the preformed catalyst-catalyst support additive composition. The resulting catalyst formulation has enhanced stability for use in the cyclic COthane process. By contrast, the incorporation of the dopant into the catalyst—support additive composition simultaneously with its formation, or the mixing of the preformed catalyst—support additive composition with the dopant prior to the addition of the binder, does not enhance the stability of the catalyst formulation. In fact, such other means of incorporating the dopant may actually reduce the stability of the resultant catalyst, and result in a generally higher level of inactive carbon formation over the course of continued use of the catalyst formulation in the practice of the COthane process. The enhanced catalyst stability obtained in the practice of the invention will thus be appreciated as representing an unexpected and highly significant advance in the desired development of improved catalysts to enhance the overall technical and economic feasability of employing the COthane process in practical commercial operations.

Apart from the particular incorporation of the dopant into the catalyst formulation, as herein disclosed and claimed, the catalyst is prepared using the materials and techniques generally as described in said U.S. Pat. No. 4,242,103 pertaining to the COthane process. The most preferred catalyst is nickel, and other generally preferred catalysts include cobalt, ruthenium, rhenium and alloys thereof. Those skilled in the art will appreciate that the transition metals including and to the left of nickel in the third row of the Periodic Table; including and to the left of rhodium in the fourth row thereof; and including and to the left of iridum in the fifth and thereof are capable of catalyzing the disproportionation reaction that comprises the first step of the cyclic, essentially two-step COthane process. For such cyclic operations that are inherently part of the economic attractiveness of the process, the catalyst will preferably be substantially in its metal state rather than in oxide form. Those skilled in the art will appreciate, however, that such catalysts are not generally available in a totally pure form, but may contain significant amounts of oxygen.

The disproportionation catalyst will typically be mixed with a catalyst support additive and with a binder as indicated in the background discussion above. The support additive is employed to support and/or disperse the catalyst, so as to prevent agglomeration and sintering thereof, thereby enhancing the activity and capacity of the catalyst in continuous commercial operations. Such catalyst support additives will generally be employed in varying amounts ranging from about 0.1 to about 95% by weight of additive based on the weight of catalyst composition mixture of catalyst and said additive. The additive is frequently employed in an amount within the range of from about 3% to about 20% by weight based on the weight of the catalyst composition mixture. Zirconia, alumina and silica and mixtures thereof are preferred catalyst support additives, with silica generally being the most preferred additive. It will be understood that silica may be employed as a catalyst support additive in a variety of forms, such as colloidal silica, hydrolyzed silica, fumed silica dioxide or such silica as produced by various known techniques and made available on a commercial basis. Those skilled in the art will appreciate that thoria and other materials, such as rare earth oxides, may be employed for catalyst support purposes. It is also within the scope of the invention to employ various combinations of support additives for the desired purpose. Each additive is preferably employed in an amount within the range of from about 3% to about 30% by weight of the catalyst composition mixture of catalyst and additive, with the combination being employed in an amount up to about 50% by weight based on the weight of said catalyst-catalyst support additive composition. A combination of silica with zirconia and/or alumina is an example of a useful support additive mixture.

Binding agents will generally be mixed with the catalyst composition in an amount within the range of from about 1% to about 40% by weight of such binder based on the total weight of the catalyst-catalyst support additive-binder mixture. While such a binder was referred to as an optional ingredient of the catalyst formulation in said U.S. Pat. No. 4,242,103, it will be appreciated that said binder forms an integral part of the catalyst formulation of the invention. The incorporation of a dopant in said binder as herein described and claimed provides the surprising enhancement of catalyst stability observed vis-a-vis the results obtained in the absence of the dopant or its incorporation other than as provided in the practice of the invention. Various binding agents known in the art may be employed in a conventional manner apart from the incorporation of the dopant therein prior to mixture with the catalyst composition. Colloidal silica is the preferred binder. Boehmite alumina, a hydrous aluminum oxide, is an example of another suitable binder.

While various catalyst-support additive combinations and methods of preparation may be determined within the skill of the art, it has been found particularly convenient to employ a coprecipitated mixture of catalyst and catalyst support additive. Thermally stable coprecipitated catalysts useful for methanation reactions have heretofore been known in the art as evidenced, for example, by the Hansford patent, U.S. Pat. No. 3,988,263, that describes the combination of catalytic materials such as nickel with alumina as a support material. The coprecipitated catalyst support additive comprises generally the hydroxide, carbonate, hydrous oxide or oxide form, or mixed phases thereof, or combinations of said oxides, or portions thereof, in which nickel or the other catalyst material and the additive are combined in a chemically reactive from, such as in the form of metallic hydrous silicates. The coprecipitated catalytically active material comprises the hydroxide or carbonate form of the catalyst material, which is thereafter reduced substantially to the metal state before use in the COthane process. For purposes of the invention, the catalytically active material should comprise from about 50% to about 99% by weight of the catalyst composition mixture of catalyst and support additive. As indicated above, nickel is the preferred catalyst, with silica being the preferred catalyst support additive, although zirconia, alumina or other suitable support additives can also be employed.

The dopant material added to the binder prior to mixing with the catalyst composition comprises an alkali or alkaline earth material conveniently in the form of a salt, such as the carbonate, hydroxide or sulfate form thereof, or an oxide. Examples of suitable alkali metal materials are sodium, potassium, and lithium. Barium and calcium are examples of suitable alkaline earth metal materials. The dopant is employed in an amount within the range of from about 0.01% to about 10%, preferably from about 0.05% to about 5%, most preferably from about 0.2% to about 0.4% by weight based on the total weight of the dopant-binder mixture.

The invention is hereinafter described with reference to illustrative examples thereof. It will be understood that such examples describe particular embodiments of the invention, but are not be be construed as limiting the scope of the invention as set forth in the appended claims.

EXAMPLE 1

A catalyst-support additive composition was prepared by the rapid addition of a 10 liter solution containing 920 gm. of sodium hydroxide in distilled water to another solution containing 2,792 gm. of nickel nitrate hexahydrate (dissolved), 250 gm. of AS-40 Ludox colloidal silica and 6.5 liters of distilled water. Solids consisting of hydrous nickel oxide, hydrous nickel silicates and silica gel were precipitated, and were filtered to remove excess liquid. The thus-precipitated and filtered solids were then repeatedly re-slurried in fresh distilled water and filtered until the filtrate reaches a pH of 6–7, at which time the sodium oxide content is minimal, i.e. less than 0.1% on a 500° C. calcined basis. The collected wet solids, comprising the catalyst-support additive composition for use in the COthane process, are dried at 100° C. The washed and dried precipitate, pursuant to the invention, was mixed with a binder after the incorporation of a dopant material into said binder. The binder-dopant formulation consisted of a solution of 1 gm. of sodium hydroxide dissolved in 10 ml. of water and added to 100 gm. of AS-40 Ludox colloidal silica. The resultant sodium precipitated silica gel slurry was added to 265 gm. of the precipitated catalyst-support additive composition powder with through agitation until the components were completely blended. The composite was carefully wetted until a consistency suitable for extrusion was obtained. The composite was then extruded as 1/16" diameter cylinders, dried at 100° C., and finally air calcined at 500° C. The resulting material contained about 68.5% NiO, 24.5% $SiO_2$ and 0.34% $Na_2O$ by weight with a 5.4% weight loss of ignition, i.e. L.O.I. The material was placed in a COthane reactor, and the catalytically active component, i.e. nickel, was reduced substantially to its metal state by the passage of a 4% hydrogen, 96% nitrogen gas steam through the reactor at 400° C. The resultant catalyst formulation was tested over the course of approximately 1800 cycles of the cyclic, essentially two-step COthane process without interruption for catalyst regeneration purposes. The results of such tests are shown in the plot of FIG. 1 of the drawings. The superior stability of the catalyst formulation of the invention is shown therein with the milliliters of methane production per gram of the catalyst formulation being on the order of 4.6 ml. after 7 cycles and remaining at about 3.4 ml. after about 1800 cycles without regeneration. After such cyclic, long term testing, it was found that the catalyst formulation had a very low residual level of inactive carbon of about 0.5% by weight based on the overall weight of said catalyst formulation. Thus, the long term stability and the capacity of the catalyst prepared in accordance with the invention are very favorable for purposes of the COthane process. As the level of catalytic activity has been found to drop after conventional burn-off for regeneration of the catalyst, such desirable long term stability and capacity are particularly significant in the development of enhanced COthane process catalyst formulations.

Other catalyst formulations made by different techniques, such as the incorporation of the dopant into the catalyst composition simultaneously with the precipitation of the catalyst-catalyst support additive composition, or the soaking of the coprecipitated catalyst-support additive in a solution of the alkali or alkaline earth metal salt, show poorer long term stability and generally higher levels of inactive carbon formation. When, on the other hand, the alkali or alkaline earth dopant is specifically added to the binder prior to mixing the binder with the precipitated and dried catalyst-support additive composition, as illustrated in Example 1, the long term stability of the final catalyst formulation, as used in the COthane process, is enhanced. In order to further evaluate the effect of adding the dopant to the pre-formed catalyst-support additive composition as compared with the practice of the invention in which the dopant is added to the binder phase prior to mixture with said composition, two catalysts were made by such techniques, using postassium as an alkali metal dopant material. The results are set forth in Examples 2 and 3 below.

EXAMPLE 2

Figure 2:
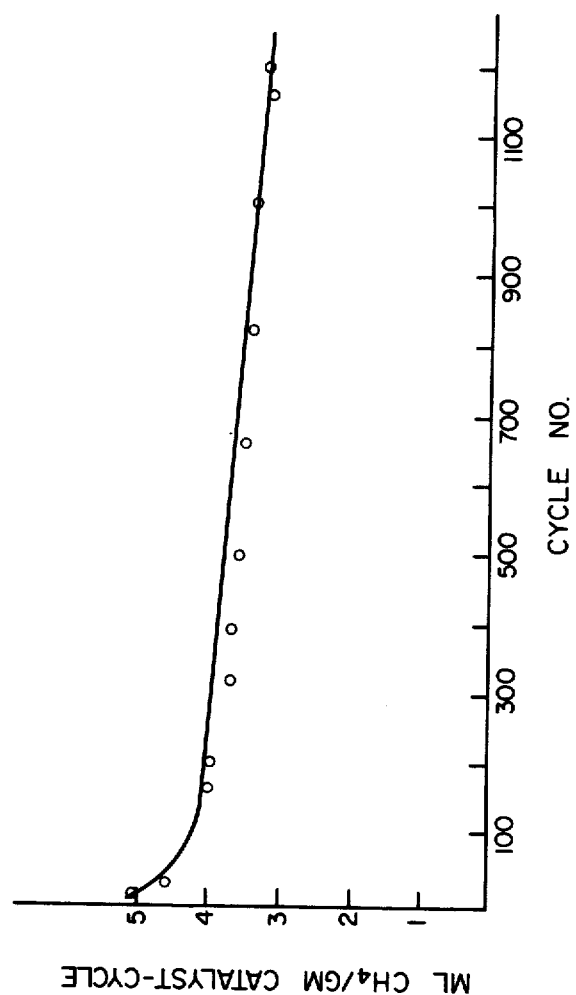
FIG. 2 is another plot similar to that of FIG. 1 but based on the use of potassium as said dopant material added to the binder in accordance with the practice of this invention.

In this example, a potassium dopant was added to the binder phase in accordance with the invention. A 4 gallon solution of distilled water containing 8,376 gm. of dissolved nickel nitrate hexahydrate and 750 gm. of AS-40 Ludox colloidal silica were rapidly added at a 5 gallon solution of distilled water containing 2,760 gm. of sodium hydroxide under agitation. The precipitated solids consisting of hydrous nickel oxides, hydrous nickel silicates and silica gel are filtered to remove excess liquid and are repeatedly re-slurried in fresh distilled water and filtered until the filtrate reaches a pH of 6–7. At this point, the sodium oxide content of the solids is minimal, i.e. less than 0.1% on a 500 C. calcined basis. The collected wet solids are dried at 100° C. The dried precipitate comprises a catalyst-support additive composition, 132.5 gm. of which is bound with a binder-dopant formulation consisting of 50 gm. of AS-40 Ludox colloidal silica gelled with 0.7 gm. of potassium hydroxide dissolved in 5 cc. of distilled water. The binder gel is thoroughly mixed with the precipitated powder. This composite is carefully wetted with distilled water until a moisture level suitable for extrusion results. The wetted composite is then extruded into 1/16" diameter cylinders, dried at 100° C., and air calcined at 400° C. for two hours. The resulting material contained 64.2% NiO, 27.1% $SiO_2$, and 0.47% $K_2O$, by weight, with a 5.4% LOI. The nickel content of the catalyst formulation was reduced substantially to its metal state by passing a gas steam containing 4% hydrogen and 96% nitrogen throught a COthane reactor containing said catalyst formulation of 400° C. The resultant catalyst formulation was employed in the cyclic, essentially two-step COthane process over the course of about 1200 cycles without regeneration to burn off or otherwise remove inactive carbon from the surface of the catalyst formulation. The results are shown in FIG. 2, indicating a stable catalyst performance at about 3.3 ml. of methane per gram of catalyst per cycle. The catalyst formulation also had a low residual inactive carbon level of 0.32% by weight. It should be noted that, although the plot of FIG. 2 appears to show an initial, relatively sharp drop in stability, this drop actually occurred over a period of about 100 cycles. The drop also will be seen to be only from 5 to about 4.25 ml. of methane produced per gm. of catalyst per cycle over such period of processing cycles. During the next 1,100 cycles, the decline in catalyst performance was very slow, i.e. the catalyst stability was very good. Over the course of the extended number of processing cycles employed, the catalyst will be seen to have an enhanced stability, as will further be evidenced by the results of Example 3 below.

EXAMPLE 3

Figure 3:
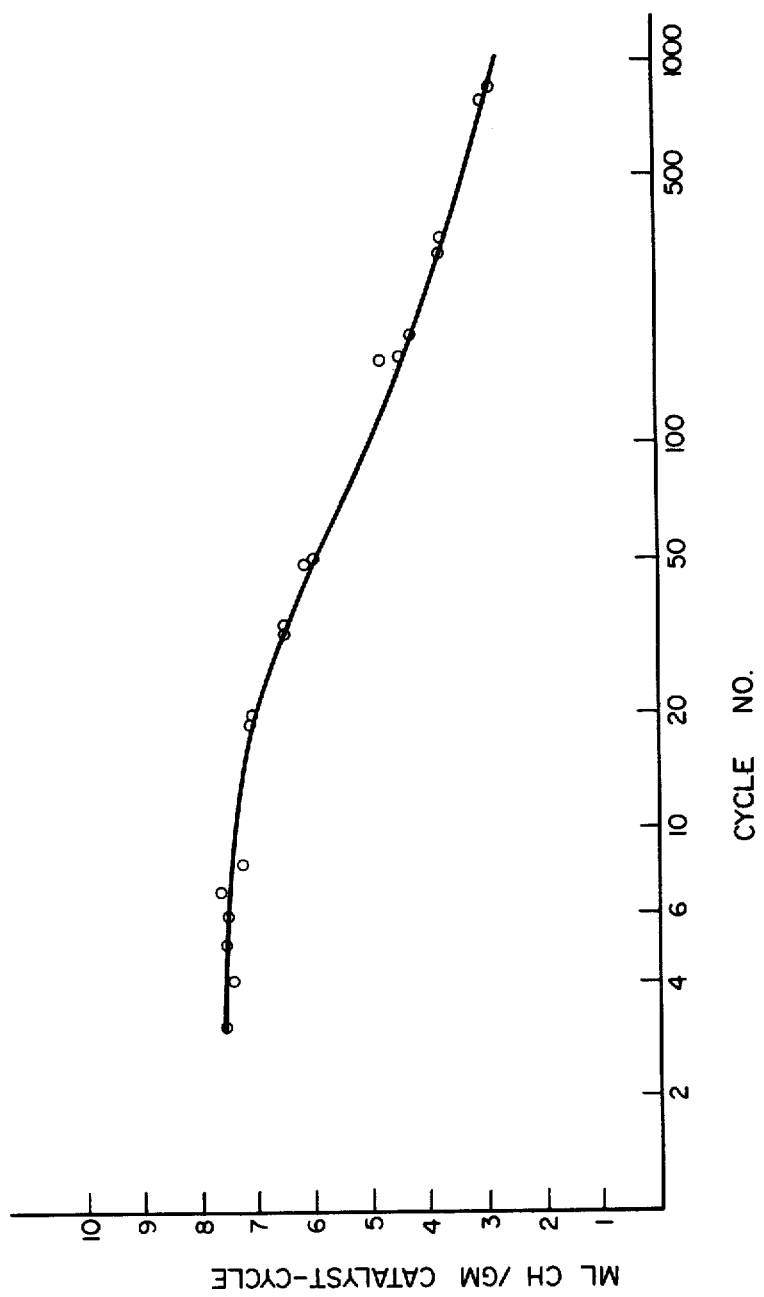
FIG. 3 is a plot similar to that of FIGS. 1 and 2 but based on the incorporation of potassium dopant material to the catalyst-support additive composition prior to the mixing of the binder with said composition.

In this example, the potassium dopant was added to the pre-formed precipitated powder comprising the catalyst-support additive composition before a binder was applied to said powder. Thus, 279.9 gm. of the precipitated nickel-silica powder synthesized as in Example 2 above was carefully slurried for 10 minutes in 2 liters of a 3% solution of potassium carbonate in distilled water. The solids were filtered and dried at 100° C. 240 gm. of the dried, potassium carbonate dopant-treated precipitate were blended with 36 gm. of Kaiser medium density alumina, which was peptized with 5 ml. of concentrated nitric acid in 36 ml. of water. The mixture was brought to any extrudable consistency with distilled water and extruded into 1/16" cylinders. The extrudates were calcined to 480° C. for two hours in dry air. The resulting unreduced catalyst product contained 70.2% NiO, 7.8% $SiO_2$, 10.8% $Al_3$, and 1.4% $K_2O$ with a 7.5% LOI. The catalyst was reduced at 400° C. with a 4% hydrogen, 96% nitrogen mixture to convert the nickel catalyst substantially to its metal state. The resulting product catalyst formulation was tested for 900 cycles of the COthane process without regeneration of the catalyst. As will be seen from the results of such tests as summarized in FIG. 3 of the drawings, the methane production using this catalyst formulation began quite high, but dropped quite rapidly after about 20 cycles, indicating a rather poor stability as compared with that obtained in the practice of the invention in Examples 1 and 2 above. This, while said methane production was initially above 7, it declined rapidly to only about 2.8 ml. of methane per gram of catalyst per cycle during the last cycle of the run. In addition, the catalyst was found to have obtained a substantial residual inactive carbon deposit level of 2.94% during said runs. The combination of poor catalyst stability, combined with a high level of inactive carbon deposition, renders the catalyst of this Example generally undesirable for use in continuous COthane process operations as compared with catalysts formulated by the process of the invention. From the greater amount of potassium dopant employed, it would have been expected, that less coking of the catalyst would have occurred.

EXAMPLE 4

To illustrate the performance of a catalyst not containing an alkali or alkaline earth metal dopant, a catalyst formulation was prepared using an alumina binder. Using a procedure similar to that of U.S. Pat. No. 3,988,263, 465.7 gm. of nickel nitrate hexahydrate, 81.38 gm. of zirconyl nitrate and 351 gm. of urea were added to 11 liters of stirred distilled water at 90° C. The pH of the solution rose from 1.80 to 6.41 over 24 hours, during which time the mixed hydrous oxides were precipitated. The solids were collected by filtration and dried at 100° C. 195 gm. of the product were mulled with 39 gm. of acid-peptized alumina, and were carefully wetted until an extrudable consistency was obtained. The composite was extruded into 1/16" cylinders, dried at 100° C., and air calcined at 450° C. The resulting catalyst, which contained 54.3% NiO, 15.6% $Al_2O_3$, and 19.1% $ZrO_2$ with a 9.8% LOI, was reduced with a hydrogen-containing stream as in the examples above. When the resulting catalyst was tested for 500 cycles of the COthane process, it showed a distinctly unstable performance, which declined sharply to 3.0 ml. of methane per gram of catalyst per cycle at the end of the test period. The catalyst was also found to contain a high residual inactive carbon content of 16% at the end of said 500 cycle test.

EXAMPLE 5

In this case as in Example 4, no dopant was employed. Silica was used as the support additive in place of alumina. A 5 liter distilled water solution containing 460 gm. of sodium hydroxide was slowly added to a rapidly stirred 5 liter distilled water solution containing 1,396 gm. of nickel nitrate hexahydrate and 125 gm. of AS-40 Ludox colloidal silica. The precipitated solids consisting of hydrous nickel oxides, hydrous nickel silicates, and silica gel were filtered and repeatedly washed to remove residual sodium hydroxide so that a sample of powder calcined at 500° C. had less than 0.1% $Na_2O$. The collected wet residue was dried at 100° C. 250 gm. of the dried powder was blended with 37.5 gm. of acid-peptized alumina used as a binder. The properly wetted composite was extruded into 1/16" cylinders, dried at 100° C., and air-calcined to 475° C. The catalyst product contained 70.0% NiO, 9.8% $SiO_2$ and 11.2% $Al_2O_3$ by weight, with a 7.0% LOI. After reduction in 5% hydrogen at 600° C., the catalyst was tested by use in the COthane process over the course of 500 cycles. It showed a nearly stable performance with a methane production rate of 3.3 ml. $CH_4$/gm. of catalyst/cycle at the end of the 500 cycle run. However, the residual inactive carbon level on the catalyst was found to be 1.1% by weight.

From such illustrative examples, it will be appreciated that the stability of the COthane process catalyst is enhanced, and the residual inactive carbon formation can be maintained at a desirably low level so that the catalyst can be used in continuous cyclic processing operations over an extended number of cycles without the need for interrupting the process for catalyst regeneration purposes. It should be noted, however, that in some embodiments of the invention the stability of the catalyst will be enhanced sufficiently to enhance the overall technical and economic feasability of the cyclic COthane process, although a very high level of inactive carbon formation may be observed. Thus, it was noted in an embodiment of the invention employing barium as the alkali metal dopant that relatively stable performance, at an acceptable methane production level, was achieved over a very long run although an unusually large amount of residual, inactive carbon was found on the catalyst. In this run, 1.2% of BaO was employed as the dopant, and the catalyst formulation was relatively stable over the course of a very long run of 4,500 cycles, despite the unusual formation of a residual inactive carbon level of 26.1% by weight. All will be appreciated from the disclosure and examples above, however, the enhanced catalyst stability of the invention is generally accompanied by very low residual inactive carbon levels, resulting in a further enhancement of the COthane process.

Those skilled in the art will appreciate that various changes and modifications can be made in particular embodiments of the invention without departing from the scope of the invention as set forth in the appended claims. Thus, while the catalyst was reduced substantially to it metal state, in the examples above, after the formation of the overall catalyst formulation, it also within the scope of the invention to so reduce the active catalyst material to its metal state prior to the mixture of the pre-formed catalyst-support additive composition with the dopant-binder mixture. As indicated on the above-indicated U.S. Pat. No. 4,242,103, the surface area of the catalyst will generally be at least about 10m$^2$/gm, preferably at least about 25m$^2$/gm, more preferably at least about 50 m$^2$/gm. When used in the practice of the COthane process, the catalysts of the invention will generally be employed in said process as developed under the contract referred to above or in conjunction with processing modifications subsequently developed with respect thereto.

The production of methane by means of the COthane process represents a significant effort to provide practical means for utilizing dilute CO-containing waste gas streams to produce low-cost, high purity methane as a replacement for natural gas. The invention, by enhancing the performance of the catalyst employed in the cyclic operation of the process, advances the feasibility of the COthane process, and thus contributes significantly to efforts to meet the energy requirements of industrial societies throughout the world.

What is claimed is:

1. An improved catalyst formulation for use in the cyclic COthane process for the production of methane from CO-containing gas streams comprising: (1) a catalyst present substantially in its metal state and capable of catalyzing the disproportionation of carbon monoxide, (2) a catalyst support additive present in an amount within the range of from about 0.1% about 50% by weight based on the total weight of catalyst and support additive, (3) a binder present in an amount within the range of from about 1% to about 40% by weight of said binder based on the total weight of catalyst-support additive-binder, and (4) an alkali or alkaline earth dopant present in an amount within the range of from about 0.01% to about 10% by weight based on the total weight of the dopant and binder employed, said catalyst formulation being prepared by the process comprising:
   (a) mixing said catalyst material and said catalyst support additive to form a catalyst-support additive composition prior to reduction of said catalyst to its metal state;
   (b) adding said dopant material to the binder to form a dopant-binder mixture prior to mixing said binder with the catalyst-support additive composition;
   (c) mixing said dopant-binder mixture with said catalyst-support additive composition; and
   (d) reducing said catalyst substantially to its active metal state,
whereby said catalyst has enhanced stability for use in the cyclic COthane process.

2. The catalyst formulation of claim 1 in which said dopant is present in an amount within the range of from about 0.05% to about 5% by weight based on the total weight of dopant and binder.

3. The catalyst formulation of claim 2 in which said dopant is present in an amount of from about 0.2% to about 0.4% by weight.

4. The catalyst formulation of claim 2 in which said catalyst support additive is present in an amount within the range of from about 3% to about 15% by weight based on the total weight of said catalyst and support additive.

5. The catalyst formulation of claim 1 in which said catalyst material comprises nickel.

6. The catalyst formulation of claim 1 in which said catalyst support additive comprises silica.

7. The catalyst formulation of claim 1 in which said binder comprises colloidal silica.

8. The catalyst formulation of claim 1 in which said dopant material comprises an alkali metal salt.

9. The catalyst formulation of claim 8 in which said alkali metal is sodium.

10. The catalyst formulation of claim 8 in which said alkali metal is potassium.

11. The catalyst formulation of claim 1 in which said dopant material comprises an alkaline earth metal salt.

12. The catalyst formulation of claim 11 in which said alkaline earth metal is calcium.

13. The catalyst formulation of claim 11 in which said alkaline earth metal is barium.

14. The catalyst formulation of claim 8 in which said alkali metal is lithium.

15. The catalyst formulation of claim 8 in which said dopant is present in an amount within the range of from about 0.05% to about 5% by weight based on the total weight of dopant and binder.

16. The catalyst formulation of claim 15 in which said alkali metal is sodium, said support additive comprises silica, and said binder comprises colloidal silica.

17. The catalyst formulation of claim 16 in which said catalyst material is nickel.

18. The catalyst formulation of claim 17 in which said dopant is present in an amount of from about 0.2% to about 0.4% by weight.

19. A process for the production of an improved catalyst formulation for use in the cyclic COthane process for the production of methane from CO-containing gas streams comprising:
   (a) mixing said catalyst and a catalyst support additive to form a catalyst-support additive composition, said catalyst not being reduced to its active metal state, said support additive being present in an amount within the range of from about 0.1 to about 50% by weight based on the total weight of said catalyst-support additive composition;
   (b) adding an alkali or alkaline earth dopant material to a binder to form a dopant-binder mixture prior to mixing the binder with said catalyst-support additive composition, said dopant being present in amount within the range of from about 0.01% to about 10% by weight based on the total weight of dopant and binder;
   (c) mixing said dopant-binder mixture with said catalyst support additive composition, said binder being present in an amount within the range of from about 1% to about 40% by weight based on the total weight of catalyst, support additive and binder; and
   (d) reducing said catalyst substantially to its active metal state, whereby the stability of the catalyst for use in the cyclic COthane process is enhanced.

20. The process of claim 19 in which said dopant is employed in an amount within the range of from about 0.05 to about 5% by weight based on the total weight of dopant and binder.

21. The process of claim 20 in which said catalyst material is nickel, said support additive comprises silica, and said binder comprises colloidal silica.

22. The process of claim 21 in which said dopant material is sodium.

23. The process of claim 21 in which said dopant material is potassium.

24. The process of claim 22 in which said dopant is employed in an amount of from about 0.2% to about 0.4% by weight based on the weight of said dopant-binder mixture.

25. The process of claim 21 in which said dopant material is calcium.

26. The process of claim 21 in which said dopant material is lithium.

27. The process of claim 25 in which said dopant is employed in an amount of from about 0.2% to about 0.4% by weight based on the weight of the dopant-binder mixture.

28. The process of claim 24 in which said catalyst support additive is employed in an amount within the range of from about 3% to about 15% by weight based on the total weight of said catalyst and support additive.

* * * * *